United States Patent [19]

Deininger et al.

[11] 4,119,730
[45] Oct. 10, 1978

[54] TREATING MUSCLE SPASMS

[75] Inventors: Rolf Deininger, Cologne; Erich Wolf, Overath, Marienlinden, both of Fed. Rep. of Germany

[73] Assignee: Chimicasa GmbH, Chur, Switzerland

[21] Appl. No.: 825,901

[22] Filed: Aug. 19, 1977

Related U.S. Application Data

[62] Division of Ser. No. 798,090, May 18, 1977, abandoned.

[30] Foreign Application Priority Data

May 18, 1976 [LU] Luxembourg .............. 74973

[51] Int. Cl.² .................................. A61K 31/09
[52] U.S. Cl. .................................. 424/341
[58] Field of Search ........................ 424/341

[56] References Cited

PUBLICATIONS

Chem. Abst. (1) 72-30079 (m) (1970).
Chem. Abst (2) 78-11566 (a) 1973.
Deut. Opoth.-Ztg. 1973 113 (30) 1159-1166.

*Primary Examiner*—Stanley J. Friedman
*Attorney, Agent, or Firm*—Kane, Dalsimer, Kane, Sullivan and Kurucz

[57] ABSTRACT

The disclosure is of an antispasmodic pharmaceutical composition which comprises an effective amount of a compound of the general formula:

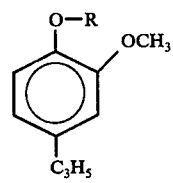

wherein R is selected from the group consisting of the acyl radical of a carboxylic acid and hydrocarbyl; and a pharmaceutically acceptable carrier.

5 Claims, No Drawings

TREATING MUSCLE SPASMS

This is a division of application Ser. No. 798,090, filed May 18, 1977, now abandoned.

BACKGROUND OF THE INVENTION

1. Field of the Invention

The invention relates to pharmaceutical compositions and more particularly relates to pharmaceutical compositions useful as antispasmodics.

2. Brief Description of the Prior Art

A number of antispasmodic compositions have been known heretofore. However, they have not been satisfactory for all purposes. For example, atropine is a well known antispasmodic but it has associated with its use a number of side effects such as the inducement of sleepiness, mental confusion and a state of inattentiveness. In many cases, especially with long term treatment, drug dependence can occur. Papaverine is another well known antispasmodic but its use in the treatment of severe spasms requires very high dosages, near the lethal dose, that is to say the dose at which a particular death rate is to be expected in animal experiments. Also, while papaverine is very active in animal experiments, when used on humans its activity is insufficient and papaverine therefore has no significance in human therapy.

The compositions of the invention are therapeutically active and are useful as antispasmodics in the treatment of muscle spasms in animals including humans. They are antispasmodics having a specific cramp-releasing action on muscles which are in a state of cramp. They are effective in a small dosage, even in the case of severe spasms.

SUMMARY OF THE INVENTION

The invention comprises an antispasmodic pharmaceutical preparation, which comprises; an effective amount of a compound of the formula:

(I)

[structure: benzene ring with O—R at position 1, OCH$_3$ at position 2, and C$_3$H$_5$ at position 4]

wherein R is selected from the group consisting of the acyl radical of a carboxylic acid and hydrocarbyl; and a pharmaceutically acceptable carrier.

The term "acyl radical of a carboxylic acid" is used herein in its conventionally accepted sense. Representative of carboxylic acid acyl radicals are the acyl radicals of the following acids:

(a) saturated or unsaturated, straight or branched chain aliphatic carboxylic acids, for example acetic, propionic, butyric, isobutyric, tert-butylacetic, valeric, isovaleric, caproic, caprylic, succinic, decanoic, dodecanoic, lauric, tridecanoic, myristic, pentadecanoic, palmitic, margaric, stearic, acrylic, crotonic, undecylenic, oleic, hexynoic, heptynoic, octynoic acids and the like;

(b) saturated or unsaturated, alicyclic carboxylic acids, for example, cyclobutanecarboxylic acid, cyclopentanecarboxylic acid, methylcyclopentenecarboxylic acid, cyclohexanecarboxylic acid, dimethylcyclohexenecarboxylic acid, dipropylcyclohexanecarboxylic acid, and the like;

(c) saturated or unsaturated, alicyclic aliphatic carboxylic acids, for example cyclopentanepropionic acid cyclohexanebutyric acid, methylcyclohexaneacetic acid, and the like;

(d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid,, phenylpropionic acid and naphthylacetic acid, and the like.

The term "hydrocarbyl" as used herein means the monovalent moiety obtained upon removal of a hydrogen atom from a parent hydrocarbon having, for example, 1 to 20 carbon atoms, inclusive.

Illustrative of such hydrocarbyl groups are alkyl of from 1 to 20 carbon aoms, inclusive, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and the isomeric forms thereof; cycloalkyl of from 3 to 20 carbon atoms such as cyclopropyl, cyclobutyl, cyclopentyl, cyclohexyl cyclohexylmethyl, cycloheptyl, cyclooctyl, 2-methylcyclopentyl, 2,3-dimethylcyclobutyl, 4-methylcyclobutyl, 3-cyclopentylpropyl, and the like; polycycloalkyl such as adamantyl and the like; aralkyl such as benzyl, phenethyl, α-phenylpropyl, phenylhexyl, phenyldodecyl, α-naphthylmethyl, and the like; alkenyl such as ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosodecenyl and isomeric forms thereof; cycloalkenyl such as cyclobutenyl, cyclopentenyl, cyclohexenyl and the like; aryl of 6 to 20 carbon atoms, inclusive, such as phenyl, o-, m- and p-tolyl, ethylphenyl, xylyl, naphthyl, diphenylyl, anthracyl, dipropylphenylyl and the like.

Those skilled in the art will appreciate that there are two isomers of each compound of the formula (I) given above. They may be schematically represented as

[structures: Isomer A — benzene ring with O—R, O—CH$_3$, and CH$_2$—CH=CH$_2$; Isomer B — benzene ring with O—R, O—CH$_3$, and CH=CH—CH$_3$]

Isomer A        Isomer B wherein R is as before defined. Both isomers are active, effective ingredients of the compositions of the invention and the formula (I) given above is intended to include both isomeric forms.

DETAILED DESCRIPTION OF THE PREFERRED EMBODIMENTS OF THE INVENTION

The essential active ingredient for the compositions of the invention are provided by compounds of the formula (I) given above. Compounds of the formula (I) are generally well known as is their preparation. In general, the compounds of formula (I) may be prepared by processes which are customary in the preparation of organic compounds, from the corresponding 4-hydroxy compounds. More specifically, in the case of esterification, the preparation of a compound (I) wherein R is an acyl radical may be carried out, for example, by the action of an appropriate acid halide or acid anhydride on 4-hydroxy-3-methoxy-1-allyl- (or -1-propenyl-) benzene in the presence of a base, for example potassium carbonate or pyridine. The procedure may be according to the well known SCHOTTEN-BAUMANN method.

In the case of etherification the preparation of compounds (I) wherein R is hydrocarbyl may be carried out, for example, by the action of an appropriate hydrocarbyl halide in alcoholic (e.g. ethanolic) solution on 4-hydroxy-3-methoxy-1-propenyl-(or-1-allyl-) benzene according to the well known WILLIAMSON synthesis.

Representative of the compounds (I) where R is the acyl radical of an aliphatic carboxylic acid are the preferred compounds 4-allyl-2-methoxyphenyl acetate, 2-methoxy-4-propenylphenyl acetate, 4-allyl-2-methoxyphenyl valerate and 2-methoxy-4-propenylphenyl valerate. Also preferred as active ingredients in the compositions of the invention and representative of those wherein R is the acyl radical of an aromatic carboxylic acid are 4-allyl-2-methoxyphenyl benzoate and 2-methoxy-4-propenylphenyl benzoate.

Of those ethers of the formula (I) wherein R is hydrocarbyl, preferred are those wherein R is lower alkyl such as 1-allyl-3,4-dimethoxybenzene and 3,4-dimethoxy-1-propenylbenzene which are preferred examples of such compounds. In the case where R is aralkyl, 2-methoxy-4-propenylphenyl-1 benzyl ether is a preferred example of such a compound.

The composition of the present invention are preferably presented for administration to humans and animals in unit dosage forms, such as tablets, capsules, powders, granules, and oral solutions or suspensions, containing effective amounts of the principal active ingredient, i.e.; a compound of the formula (I), supra.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, starch, lactose, acacia, methylcellulose, and functionally similar materials as pharmaceutical diluents or carriers. In their simplest embodiment, capsules, like tablets, are prepared by mixing the principal active ingredient with an inert pharmaceutical diluent and filling the mixture into a hard gelatin capsule of appropriate size. Soft gelatin capsules are prepared by machine encapsulation of a slurry of the principal active ingredient with corn oil, light liquid petrolatum or other inert oil.

Fluid unit dosage forms fororal administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar, saccharin, and cyclamate together with an aromatic flavoring agent. Suspensions can be prepared of the insoluble forms with a syrup vehicle with the aid of a suspending agent such as acacia, tragacanth, methylcellulose and the like.

The term "unit dosage form" as used in the specification and claims refers to physically discrete units suitable as unitary dosages for human subjects and animals, each unit containing a predetermined quantity of active material calculated to produce the desired therapeutic effect in association with the required pharmaceutical diluent carrier or vehicle. The specifications for the novel unit dosage forms of this invention are dictated by and directly dependent on (a) the unique characteristics of the active ingredient material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, troches, suppositories, powder packets, granules, wafers, cachets, teaspoonfuls, tablespoonfuls, dropperfuls, ampuls, vials, segregated multiples of any of the foregoing, and other forms as herein described.

The dosage of active ingredient, i.e.; a compound of the formula (I) above depends on route of administration; the age, weight and condition of that patient. For adults, a dosage schedule of from about 5 mg. to 500 mg., as required, usually embraces the effective range for the treatment of most conditions.

The effective amount of a compound (I) required for administration to a mammal suffering from spasms is within the range of from about 1 mg. per kilogram of body weight to about 50 mg. per kilogram of body weight, of recipient, as required.

The following examples describe the manner and process of making and using the invention and set forth the best mode contemplated by the inventor of carrying out the invention but are not to be construed as limiting.

The antispasmodic effect of the compounds (I) could not be expected from a study of their structure alone. Their effectiveness has been measured in a pharmacological standard test as follows:

Several 3 cm-long pieces of an isolated guinea pig intestine were stretched under a load of 0.5 g in separate baths. In all baths, the bath liquid was Tyrode's solution, warmed to 32° C. A first contraction of the pieces of intestine was produced in each case by adding 0.5 mg (milligram) of histamine chloride per liter of bath liquid. he reduction in length caused by the first contraction was measured 2 min (minutes) after adding the histamine chloride.

The bath liquids were then renewed and, after relaxation of the first contraction, the agent under test, dissolved in propylene glycol, was added to the bath liquids and 2 min later 0.5 mg. of histamine chloride per liter of bath liquid was again added. A second contraction was thereby produced and the reduction in length caused by this was measured 2 min after the addition of the histamine chloride. It was found that the second contractions, as compared with the first contraction, were inhibited by the agent added. The concentrations $(ED_{50})$ of agent per liter of bath liquid, which inhibit the contraction of the intestine by 50% were determined ($ED_{50}$ = effective dose to inhibit for 50%). The values found are given in Table 1.

TABLE 1

| Agent Compound of Formula (I) | $ED_{50}$ (mg/liter) |
|---|---|
| 4-Allyl-2-methoxyphenyl acetate | 25.0 |
| 4-Allyl-2-methoxyphenyl butanoate | 14.5 |
| 4-Allyl-2-methoxyphenyl valerate | 44.6 |
| 4-Allyl-2-methoxyphenyl benzoate | 160.0 |
| 1-Allyl-3,4-dimethoxybenzene | 11.8 |
| 3,4-Dimethoxy-propenylbenzol | 27.0 |

TABLE 1-continued

| Agent Compound of Formula (I) | ED$_{50}$ (mg/liter) |
| --- | --- |
| 2-Methoxy-4-propenylphenyl acetate | 52.0 |

In accordance with the spasmolytic effectiveness proved by the pharmacologic test we have found that the named compounds also have a specific cramp-releasing action on the human organism and display a significant antispasmodic action in a small dosage even in the case of a very severe attack of cramp. Unpleasant side effects, at any rate to the extent to be expected in the case of known antispasmodic agents, were not observed. The antispasmodic action occurred both after oral administration and after rectal administration, which is a further advantage. Non-specific actions, such as are observed in the case of papaverine, do not occur.

The effectiveness of the compositions of the invention is illustrated in the following examples.

EXAMPLE 1

100 g of 4-allyl-2-methoxyphenyl acetate are put in a tray of corrosion-proof steel and warmed within a water bath to a temperature of 45° C. The acetate melts. The molten mass is tempered to 40° C. and under stirring and further warming 2 300.0 g of physiologic neutral suppository mass is added. A triglyceride mixture of saturated straight chain vegetable fatty acid of a chain length of $C_{12}$–$C_{18}$ and a melting point of 32°–33.5° C. is used as the suppository mass.

After melting thoroughly and homogenizing, the mass is cooled to 36°–38° C. and poured into molds for suppositories. The mass is solidified by cooling to room-temperature. The obtained suppositories having a weight of 2.4 g are loosened from the molds and kept ready for the examination of the antispasmodic effectiveness of 4-allyl-2-methoxyphenyl acetate on humans.

The effectiveness test is performed by cystometric measuring of the damping of the increase of the bladder tonus caused by the antispasmodic agent after intravesical administration of a spasmogenic agent as follows:

The bladder capacity (BC) of several human subjects with indwelling permanent catheters is measured by filling the bladders with water warmed to 37° C. The maximum micturition pressure (MM) in the case of the filled bladder is measured. The bladder is then emptied and filled again with warm, clean water to half the capacity measured previously (½ BC) and the pressure P1 in the case of the half-filled bladder is measured. The bladder is again emptied and filled again to half its capacity with a solution 1. The solution 1 consists of clean water, warmed to 37° C., in which 1.76 g of carbachol, a spasmogenic agent, is dissolved per liter of water. The pressure P2 for half its capacity is measured. The bladder is then again emptied and 100 mg of 4-allyl-2-methoxyphenyl acetate administered rectally into the rectum of the experimental subjects in the form of one of the suppositories. 30 minutes thereafter the emptied bladder is filled with water, warmed to 37° C. to half its capacity and the pressure P3 is measured. The bladder is subsequently emptied and filled to half its capacity with the solution 1 and the pressure P4 is measured. Fifteen minutes later, the bladder is emptied again and filled to half its capacity with water, warmed to 37° C. and the pressure P5 is measured. Directly thereafter, the bladder is emptied and filled to half its capacity with solution 1 and the pressure P6 is measured. The measured values are given in Table 2, below.

The micturition pressure is the internal bladder pressure required to cause emptying of the bladder. All pressures P1 to P6 given are micturition pressures.

TABLE 2

Measured values on rectal administration of 100 mg of 4-allyl-2-methoxyphenyl acetate.

| Experimental Subject No. | BC | MM | P1 | P2 | P3 | P4 | P5 | P6 |
| --- | --- | --- | --- | --- | --- | --- | --- | --- |
| 1 | 200 | 59 | 0 | 19 | 0 | 6 | 0 | 9 |
| 2 | 300 | 60 | 2 | 16 | 0 | 0 | 0 | 0 |
| 3 | 300 | 56 | 0 | 5 | 0 | 2 | 0 | 5 |
| 4 | 400 | 80 | 6 | 10 | 0 | 2 | 0 | 1 |
| 5 | 400 | 85 | 0 | 40 | 0 | 6 | 0 | 2 |
| 6 | 300 | 72 | 3 | 32 | 1 | 9 | 2 | 10 |
| 7 | 400 | 57 | 0 | 6 | 0 | 1 | 0 | 2 |
| 8 | 200 | 40 | 1 | 5 | 0 | 0 | 0 | 0 |
| 9 | 200 | 45 | 2 | 14 | 0 | 0 | 0 | 0 |
| 10 | 200 | 70 | 2 | 31 | 0 | 0 | 0 | 0 |
| 11 | 200 | 32 | 2 | 6 | 0 | 1 | 0 | 1 |
| 12 | 200 | 50 | 0 | 7 | 0 | 1 | 0 | 1 |
| 13 | 300 | 37 | 0 | 6 | 0 | 1 | 0 | 1 |
| 14 | 300 | 79 | 2 | 12 | 0 | 2 | 0 | 7 |
| 15 | 200 | 51 | 0 | 10 | 0 | 4 | 0 | 4 |

EXAMPLE 2

The procedure of Example 1, supra, is followed with the only difference that instead of 100 g of 4-allyl-2-methoxyphenyl acetate, 50 g of 1-allyl-3,4-dimethoxybenzene are mixed into 2 350.0 g of the suppository mass. The obtained suppositories with a weight of 2.4 g contain 50.0 mg of 1-allyl-3,4-dimethoxybenzene. Ten experimental subjects are treated as in Example 1 by using the latter suppositories. The measured values are given in Table 3 below.

TABLE 3

Measured values on rectal administration of 50 mg of 1-allyl-3,4-dimethoxybenzene.

| Experimental Subject No. | BC | MM | P1 | P2 | P3 | P4 | P5 | P6 |
| --- | --- | --- | --- | --- | --- | --- | --- | --- |
| 21 | 300 | 60 | 0 | 22 | 0 | 2 | 0 | 4 |
| 22 | 400 | 55 | 1 | 8 | 0 | 0 | 0 | 2 |
| 23 | 300 | 85 | 0 | 15 | 1 | 0 | 0 | 0 |
| 24 | 200 | 57 | 3 | 10 | 0 | 2 | 1 | 2 |
| 25 | 200 | 70 | 2 | 32 | 1 | 6 | 1 | 4 |
| 26 | 400 | 37 | 0 | 12 | 0 | 2 | 0 | 0 |
| 27 | 500 | 52 | 0 | 10 | 0 | 0 | 0 | 0 |
| 28 | 350 | 45 | 1 | 14 | 0 | 1 | 0 | 1 |
| 29 | 300 | 65 | 2 | 23 | 2 | 1 | 1 | 1 |
| 30 | 300 | 48 | 2 | 12 | 0 | 1 | 0 | 2 |

EXAMPLE 3

10.0 g of 4-allyl-2-methoxyphenyl acetate is warmed to 40° C. in a tray of corrosion-proof steel, 10.0 g of disperse silicic acid (with 99.8% of $SiO_2$ and a density of 60 g/l) and 10.0 g of maize starch are then added under stirring. Thereafter the powdery mixture is pressed five times through a 100 μm mesh sieve, to secure the equipartition of the acetate within the powdery mixture. A 300 mg portion of this homogeneous mixture is filled into hard gelatine capsules. Each of the capsules contain 100 mg of 4-allyl-2-methoxyphenyl acetate and serve for oral administration to humans.

Five human subjects are treated according to the general procedure of Example 1, with the difference that instead of rectal administration of the agent, one of the above capsules are orally administered. The measured values are given in Table 4, below.

TABLE 4

Measured values on oral administration of 100 mg of 4-allyl-2-methoxyphenyl acetate.

| Experimental Subject No. | BC | MM | P1 | P2 | P3 | P4 | P5 | P6 |
|---|---|---|---|---|---|---|---|---|
| 1 | 400 | 80 | 15 | 55 | 22 | 32 | 13 | 18 |
| 2 | 500 | 50 | 5 | 10 | 7 | 7 | 5 | 7 |
| 3 | 350 | 75 | 22 | 30 | 20 | 25 | 20 | 22 |
| 4 | 600 | 66 | 15 | 25 | 20 | 23 | 12 | 15 |
| 5 | 400 | 55 | 5 | 17 | 12 | 15 | 8 | 10 |

In all examples there has been set a cramp by the carbachol of the Solution 1. This is shown by the fact that the values of P2 are greater than the values of P1. This cramp was released totally by the rectally administered composition of the invention and considerably reduced by the orally administered composition of the invention, as it is shown by the values of P3 and P5 within all examples. The compositions of the invention even has an effect against the direct action of the carbachol still present in the bladder. This is shown by the fact that the values P4 and P6 are lower than the values of P2. The values of P3 and P5 show that 30 minutes respectively 45 minutes after the administration of the composition of the invention, a considerable cramp-releasing action was obtained. Especially these values show the remarkable effectiveness of the compositions of the invention used according to these examples on humans.

The examples specifically show the effectiveness of 4-allyl-2-methoxyphenyl acetate after rectal or oral administration and of 1-allyl-3,4-dimethoxybenzene after rectal administration on humans.

The clinical correlative of the test results according to the above examples is in the therapeutic effectiveness on spasms of the smooth muscular system as arterial and venous circulatory disturbance, Angina pectoris, asthma, spastic bronchitis, stomach spasms and intestinal spasms, unspecific irritation of bladder, renal and bilious colics, menstruation complaints and abortion of gallstones, renal stones and bladder stones, obtained by administrations to mammals afflicted with these conditions, an effective amount of a composition of the invention.

What is claimed:

1. A method of treating muscle spasm in a mammal, which comprises; administering to the mammal a unit dose form of a therapeutic composition, which comprises; a compound of the formula:

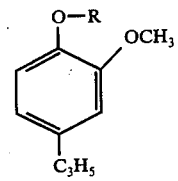

wherein R is selected from the group consisting of alkyl of from 1 to 20 carbon atoms, inclusive, cycloalkyl of from 3 to 20 carbon atoms, inclusive, polycycloalkyl having up to 20 carbon atoms, aralkyl having 7 to 20 carbon atoms, inclusive, and aryl having 6 to 20 carbon atoms, inclusive; and a pharmaceutically acceptable carrier.

2. The method of claim 1 in which R is selected from alkyl and aralkyl.

3. The method of claim 2 in which R is methyl.

4. A method of claim 1 wherein the compound is 1-allyl-3,4-dimethoxybenzene.

5. The method of claim 1 wherein the compound is 4-allyl-2-methoxyphenyl acetate.

* * * * *